US007309347B2

(12) United States Patent
Cuccia

(10) Patent No.: US 7,309,347 B2
(45) Date of Patent: Dec. 18, 2007

(54) FOOT AND CALF SUPPORT AND ADJUSTMENT ASSEMBLY

(76) Inventor: David F. Cuccia, 227 Jackson Ave., Syosset, NY (US) 11791

( * ) Notice: Subject to any disclaimer, the term of this patent is extended or adjusted under 35 U.S.C. 154(b) by 329 days.

(21) Appl. No.: 11/189,956

(22) Filed: Jul. 25, 2005

(65) Prior Publication Data

US 2005/0256538 A1 Nov. 17, 2005

Related U.S. Application Data

(63) Continuation of application No. 10/413,730, filed on Apr. 15, 2003, now Pat. No. 6,923,825, which is a continuation-in-part of application No. 09/661,078, filed on Sep. 13, 2000, now Pat. No. 6,547,809.

(51) Int. Cl.
*A61F 5/00* (2006.01)

(52) U.S. Cl. ...................... 606/244; 606/241; 606/242

(58) Field of Classification Search ................ 606/237, 606/241, 242, 243, 244, 245; 602/32–36; 601/23, 24, 26; 482/112, 113, 142; 5/612, 5/618, 658, 662; 128/845
See application file for complete search history.

(56) References Cited

U.S. PATENT DOCUMENTS

| | | | | | |
|---|---|---|---|---|---|
| 2,023,429 | A | * | 12/1935 | Lorang | 606/245 |
| 2,267,054 | A | * | 12/1941 | Thompson | 606/245 |
| 5,176,706 | A | * | 1/1993 | Lee | 606/237 |
| 5,794,286 | A | * | 8/1998 | Scott et al. | 606/240 |
| 5,860,899 | A | * | 1/1999 | Rassman | 606/242 |
| 6,547,809 | B1 | * | 4/2003 | Cuccia | 606/242 |
| 6,923,825 | B2 | * | 8/2005 | Cuccia | 606/244 |

* cited by examiner

*Primary Examiner*—Quang D. Thanh
(74) *Attorney, Agent, or Firm*—Melvin K. Silverman; Yi Li

(57) ABSTRACT

A calf/foot support and treatment table for extension, flexion, traction, distraction and lateral movement of the body of a patient includes a base adapted to rest upon a floor, and a system support assembly having an upper end and a lower end integrally secured to the base, a rigid support platform having a lower part and an upper part, the support platform pivotally secured to a pivot axle of said system support assembly; a lumbar support assembly disposed on the lower part of the support platform; and a calf/foot support assembly for linear traction.

17 Claims, 12 Drawing Sheets

FOOT AND CALF SUPPORT AND ADJUSTMENT ASSEMBLY

REFERENCE TO RELATED APPLICATION

This application is a continuation of patent application Ser. No. 10/413,730, filed Apr. 15, 2003, now U.S. Pat. No. 6,923,825, which is a continuation-in-part of application Ser. No. 09/661,078, filed Sep. 13, 2000, now U.S. Pat. No. 6,547,809. All prior applications are hereby incorporated by reference in their entirety.

BACKGROUND OF THE INVENTION

The within invention is an improvement of the inventions of my U.S. Pat. No. 4,915,101 (1990), U.S. Pat. No. 5,922,011 (1999), and that reflected in my application Ser. No. 09/661,078, filed Sep. 13, 2000.

Numerous devices, including chiropractic, osteopathic, obstetrical, delivery, x-ray and operating tables, which suspend or position a patient in a unique way for some special purpose, are known in the art.

U.S. Pat. No. 4,568,669 (1971) to Stiles discloses a posture board wherein the patient is rotated 180 degrees from an initial upright position on his back to one of complete inversion hanging by the ankles. With the body hanging freely, normal gravitational pull is reversed thus causing a therapeutic effect on bone structure, spinal column, muscles, internal organs and body fluids. U.S. Pat. No. 4,103,681 (1978) to Shanley similarly discloses a tilting traction apparatus where the patient, again lying on his back, is rotated about a pivot point to treat back injury or postural misalignment.

U.S. Pat. No. 4,292,926 (1981) to Krause presents an apparatus for effecting postural treatment of humans in which the patient, while resting face down on a pivoting platform, can vary the position of his arms, adjust his center of gravity while in suspension and, thereby, affect his posture upon the table.

It is to be appreciated that the success of any device designated to treat lower back dysfunction is in large part dependent on proper positioning of the patient prior to, during, and after treatment. For example, in standard traction therapy, the patient wears a pelvic harness and is positioned supinely (face up) in bed, with the spine slightly flexed and knees bent. Straps or roping which is attached to the harness are then inserted into a pulley mechanism and weights attached at an opposite end, causing a desired pulling/traction effect. Such pulling traction force produces an elongation of the spinal column (distraction) and a reduction in internal intervertebral disc pressure. This creates a vacuum phenomenon inside the disc, which retracts protruded gelatinous material back into its fibrous casing and off of the spinal nerve roots. With the pain gone and the anatomy restored to its natural state, the traction phase of therapy is complete.

An alternate theory for accomplishing the same result is based on extension, rather than flexion of the spine, to achieve reduced intradiscal pressure, while simultaneously anatomically moving nerve roots away from the herniated disc.

While the general principles of flexion and axial traction of the spine are known in the art and have been effected in various strap and/or harness arrangements, either alone or in combination with rotating-pivot type tables as are described above, the inventor has found that both flexion and extension, as well as lateral positioning with traction, can all be beneficial depending upon the patient's particular ailment or condition.

As such, there exists a need for a system which combines varying degrees of both traction or distraction with concomitant patient position flexion, extension, lateral flexion, and or axial spinal positioning. The present invention being both beneficial to the patient and convenient to the doctor, fulfills this need in a variety of ways in that the inventive treatment table not only enables rotation of a patient about a pivot point but, additionally, permits the relative, selectable positioning of the patient's arms, upper torso, legs, lower back, head and shoulders through manual adjustment or an automatic keypad control. The present invention also allows a complete choice as to prone, supine or lateral positioning of the patient prior to treatment. It further enables the doctor to vary the position of the patient prior to and during treatment, and to vary the degree of tractive force applied to the patient by selectably variably rotating the patient platform to increase or decrease the tractional gravitational pull applied through such rotation. There is further provided a "dynamic rotation" into a variable vertical traction position, i.e., the patient stands upright against the table, supported by an adjustable shoulder, arm and hand support and is lifted off the ground, thereby achieving tractional dynamics related to those described above, namely a rapid lengthening of the muscles and longitudinal ligaments of the spine increasing the separation of the intervertebral disc and articular joint spaces. This results in both mobilization of the spine and rapid development through the "disc unloading" of a negative internal disc pressure responsible for causing the vacuum phenomenon for retracting protruding disc material back within the borders of a healthy disc while keeping the patient suspended in mid-air, or while the patient remains standing on a weighted patient platform, utilizing the weight of the lower extremity, the force of gravity, and selected patient anatomical positioning.

My instant invention therefore defines functionally over the structure of my earlier inventions in the following material respects:

1. Ability to concurrently or sequentially lift and rotate the patient, thus providing various treatment options to the physician, including more effective traction of vertebral segments prior to and during table and patient rotation, thereby reducing stress on articulate vertebral surfaces of the patient and obtaining a generally more ergonomic patient interface.
2. Ability to change radius of lower back support assembly, to effectuate varying degrees of lumbar extension and lumbar support, as well as a general mobilization of the lumbar spine (lower back).
3. Ability to tilt, at a variety of angles, the top or bottom half of the lower back support assembly, allowing a greater range of positions of the patient's lumbar spine, and to increase or decrease the lumbar lordosis.

SUMMARY OF THE INVENTION

A foot and calf support and treatment table for extension, flexion, traction, distraction and lateral movement of the spine and lower body of a patient is provided. The table more particularly includes a base adapted to rest upon a floor, and system support means having an upper end and a lower end integrally secured to said base, said support means including a pivot axis proximal to said upper end thereof. The treatment table also includes means for selectable reciprocal extension having an upper end and a lower end, one end pivotally attached to said system support means, said selectable extension means providing reciprocal movement of said one end relative to an opposite end thereof. The table further includes a rigid support platform having an upper end and a lower end, said platform pivotally secured to said pivot axis of said support means and, further, pivotally secured to said one end of said selectable extension means, thereby providing a resultant rotational motion of the support platform. The treatment table yet further includes a body support assembly adjustably positionable relative to said rigid support platform, said assembly having an upper end and a lower end; and means for enabling said patient to remain on said body support assembly during rotational movement thereof.

A principal object of the invention is to provide a multi-purpose table to effectuate flexion, extension, traction, lateral movement and distraction of the spine, as may be required in the treatment of spinal disorders and/or maintenance of proper human posture, in such a manner that the relative positions of the patient's arms, legs, lower back, head and shoulders can be varied.

Another object is to provide a multipurpose rotatable traction/treatment table permitting patient rotation and dynamic lifting of a patient while standing, concurrently with selective patient body positionings as may be required in the treatment of disc herniations and other disorders and/or maintenance of proper human posture.

Yet another object of the invention is to provide a treatment table having a range of motion from zero to at least ninety degrees and, within that range, which can pivot from zero to at least ninety degrees, thereby providing the ability to achieve spinal positioning including spinal flexion, extension, lateral flexion, and axial spinal positioning and traction in the absence of a lower leg support assembly enabled by inherent torso support and placement of the human body at or near its center of gravity at the lower back support assembly.

A still further object is to provide a table which having a variety of pneumatic and other adjustments to permit that patients of widely disparate age, height and weight to be accommodated, without requirement of extended physician set up time.

Another object of the invention is to provide a multipurpose table that is simple to operate, weighted and designed for safety so as not to tip, and constructed of quality materials.

A yet further object is to provide a system in which the position of the upper torso support assembly may be varied relative to the lower back support assembly.

It is another object to provide a system than can concurrently or sequentially lift and/or rotate the patient, this providing various treatment options to the physician, including more effective and safer traction of vertebral segments.

DETAILED DESCRIPTION OF THE INVENTION

Figure 1:
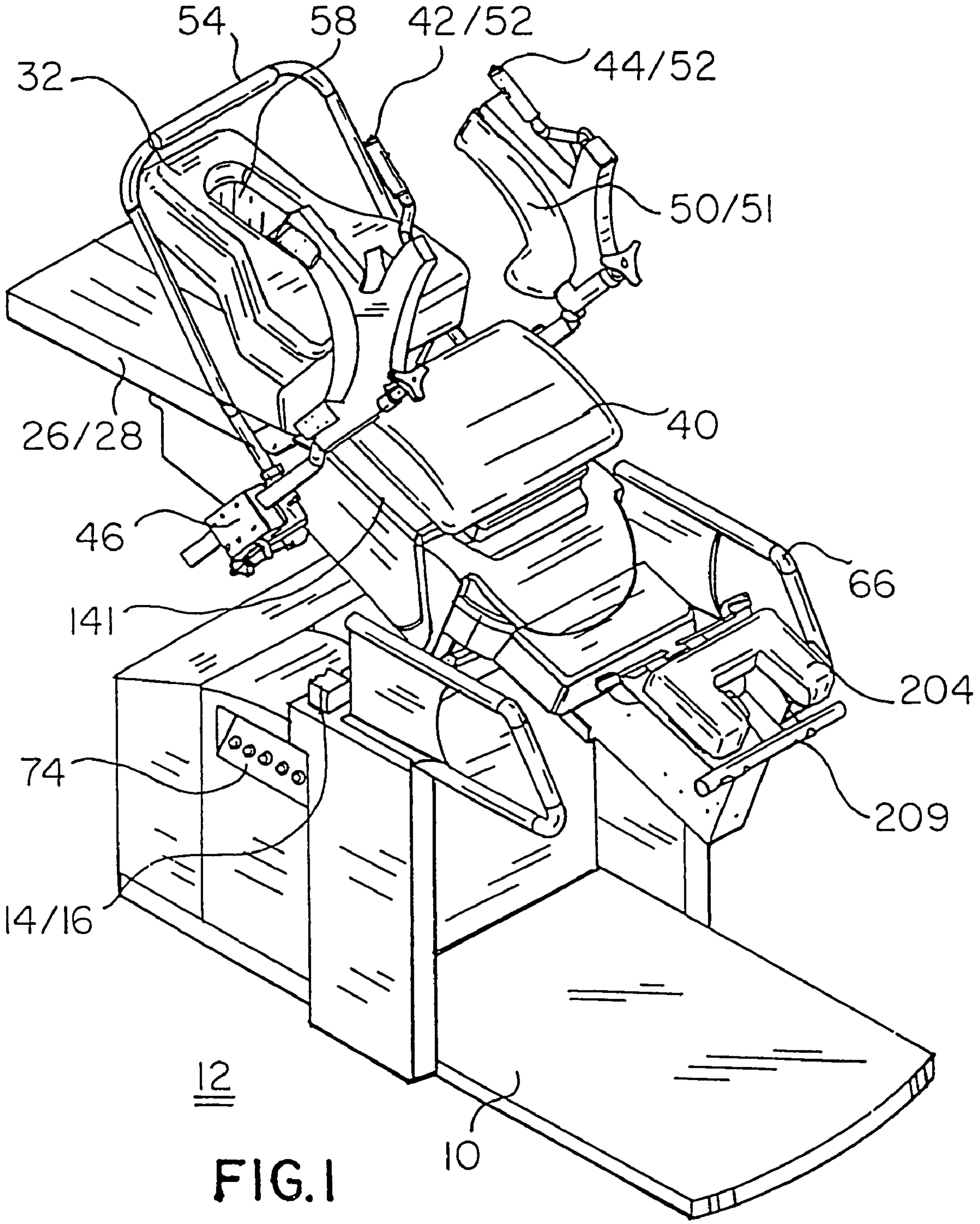
FIG. 1 is a front perspective view of the inventive multifunction chiropractic treatment table.
Figure 2:
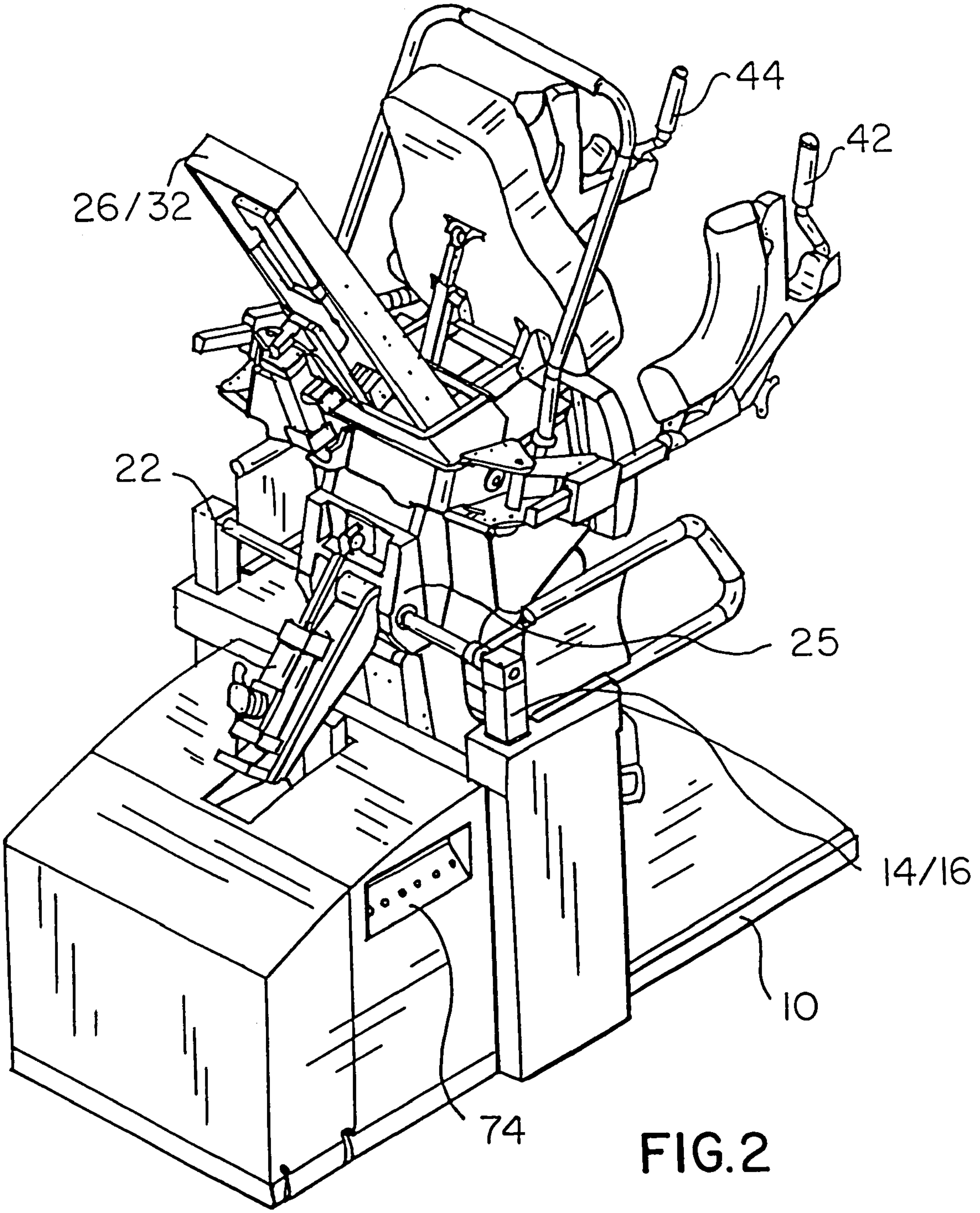
FIG. 2 is rear diagonal perspective view thereof.

With reference to the views of FIGS. 1 and 2, the present chiropractic treatment table for effecting extension, flexion, traction and distraction of the spine of a patient, to which the invention relates, may be seen to include a base 10 adapted to rest upon a floor 12 in a typical treatment room of a chiropractor, physical therapist, or other health professionals involved in physical medicine. The chiropractic table may be seen to optionally include a pair of elevation means 14 and 16 to enable positioning of patients of various heights on the table. Elevation means 14 and 16 preferably comprise extensible hydraulic pistons, each including upper ends which support a pivot axle 22.

Figure 3:
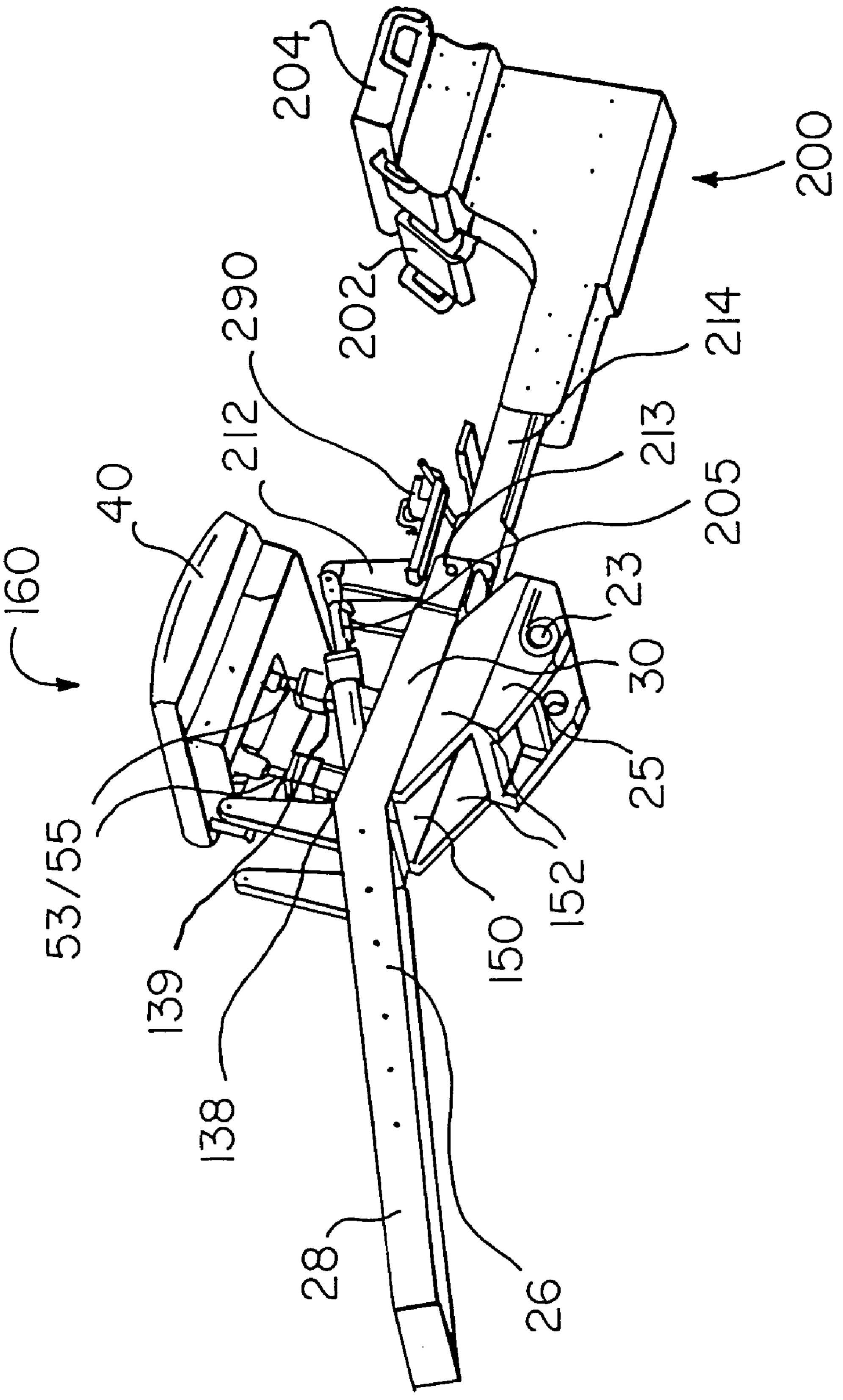
FIG. 3 is a general side perspective view of the lumbar back support and calf and foot support assemblies.

As may be appreciated in the view of FIG. 3, pivot axle 22 is journalled within channel 23 of block support 25 of rigid upper body support platform 26.

The instant multi-purpose treatment table thereby includes said upper support platform 26 having an upper part 28 and a lower part 30. Said lower part 30 of rigid support platform 26 is secured to said pivot block 25 (see FIG. 3) which is rotatable upon said pivot axle 22 at the approximate mid-point of lower part 30 of platform 26. As may be further noted, said upper part 28 defines a plane which is directed at an angle of about thirty degrees relative to a plane defined by said lower part 30 of the upper support platform 26. Such an angle is necessary in that it allows the patient's upper body to be ergonomically supported by a body support assembly 32 (See FIG. 1), permitting the back to extend convexly and backward relative to base 10. Support assembly 32 is mounted upon said upper part 28 of said rigid support platform 26. Said body support assembly may or may not be divided into, and may or may not include, moveable sections with hydraulic or pneumatic pistons or other means for elevation and de-elevation of the body support assembly 32. Said body support assembly may contain an integral air bladder for additional immobilization.

With reference to FIGS. 1 and 2, the system may also be seen to optionally include a pair of positionally adjustable arm support means 42 and 44 which are located proximally to the sides of a body support assembly 32. As is set forth below, said arm support means include a selectably adjustable rear portion 46 which is secured to said upper part 28 of the rigid support platform 26. Said arm support means 42 and 44 include (i) substantially horizontal arm rests 50; (ii) a chest and shoulder support 51 situated posteriorly and angled inwardly in a patient direction from said arm rest; and (iii) a tilted hand grip 52 depending integrally upwardly and inwardly, proximally to said chest and shoulder supports 51.

The present treatment table may be seen to further include a lumbar and buttock support assembly 40, which is displaced from said body support assembly 32. Lumbar assembly 40 is connected to telescoping piston rods 53 and 55 (see FIG. 3) or other means which provide for elevation and de-elevation thereof. Said lumbar assembly may include an internal air cushion in the form of an inflatable air bladder, for added support and tissue mobilization. The same is true of the upper torso support assembly. Foot-and-calf assembly control bar 209 and foot rest 204 may also be seen in FIG. 1.

In FIG. 3 is shown a general view of lumbar back assembly 160 and of calf/foot support assembly 200. Therein, said figure depicts a general position of the lumbar support assembly in relation to the calf/foot support assembly and rigid support platform 26, including upper and lower portions of 28 and 30 respectively, associated with the platform 26. Also, shown in FIG. 3 is lumbar cushion 40 and lumbar cushion hydraulic/pneumatic extension rods 53/55 which, in combination with hydraulic pistons 138/139, determine the angle of the lumbar cushion relative to lower portion 30 of the rigid support platform 26. Said cylinders 138/139 rest upon a rigid support frame plate 150 which itself is supported by a rigid support frame space bar 152 and a block support 25 which includes a main horizontal axial channel 23 through which pivot axle 22 (see FIGS. 1 and 2).

Further shown in FIG. 3 is calf/foot support link casting 212, foot tubing 214, foot rest 202 and ankle cushion 204, all of calf/foot support assembly 200. Also shown therein is side-swing mechanism 290 of calf/foot support assembly 200.

Figure 4:
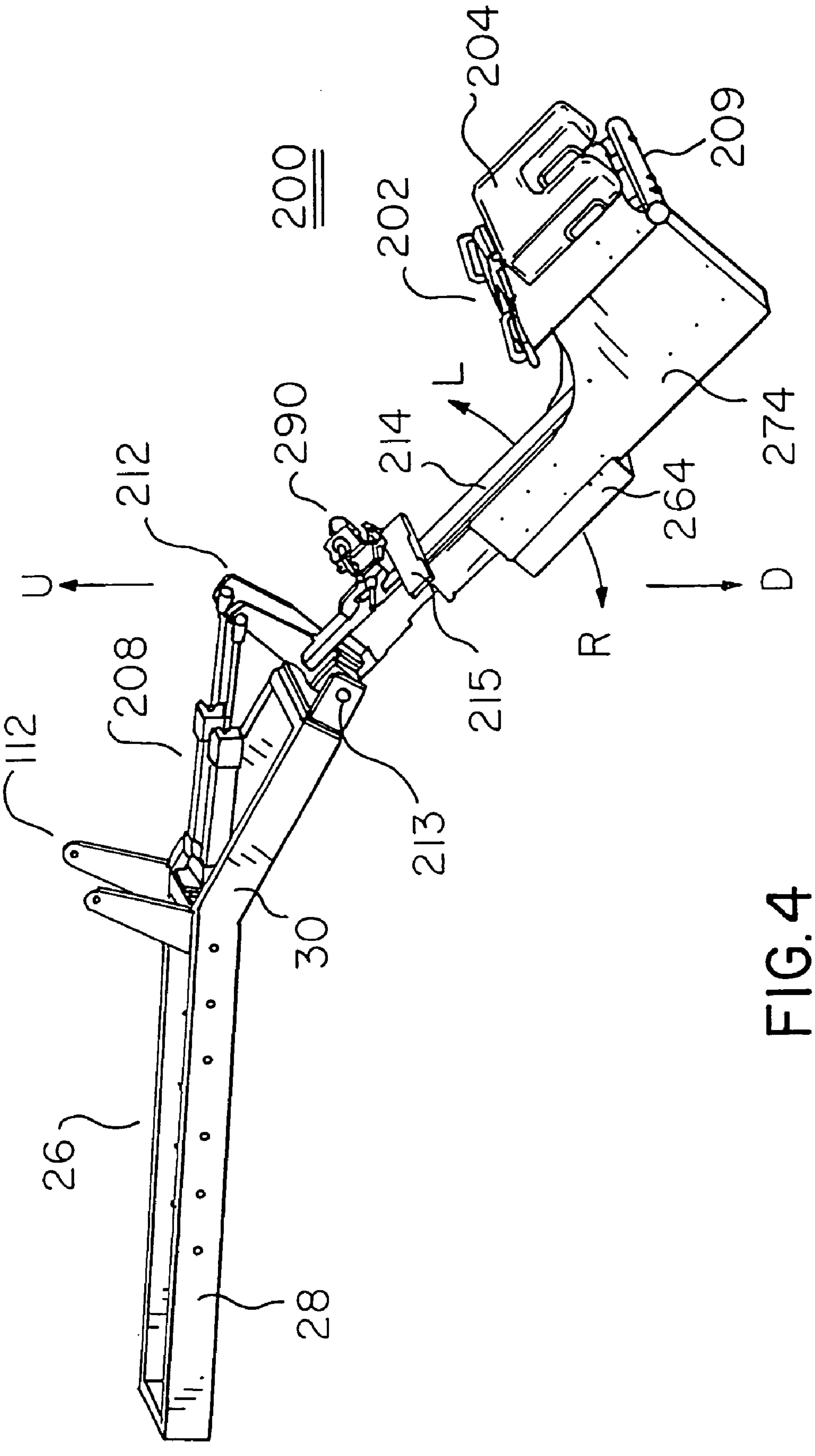
FIG. 4 is a perspective view showing the vertical positioning of the calf/foot support assembly.

In FIG. 4 is a more detailed illustration of the calf/foot support assembly and its relationship to rigid support platform 26. More particularly, therein are shown calf/foot support assembly vertical positioning hydraulics 208 and their relationship to said calf/foot support link casting 212 and lumbar support casting 112. Also shown is link casting axle 213 of the calf/foot support link casting 212, said side-swing assembly 290 and its transverse bar 215, foot tubing 214, foot side bracket 274, foot lock housing 264, foot rest 202, ankle cushion 204, and calf/foot support assembly control bar 209. Also shown therein are arrows U, D, R, and L which illustrate the up-down and left-right degrees of freedom of the calf/foot support assembly 200.

Figure 5:
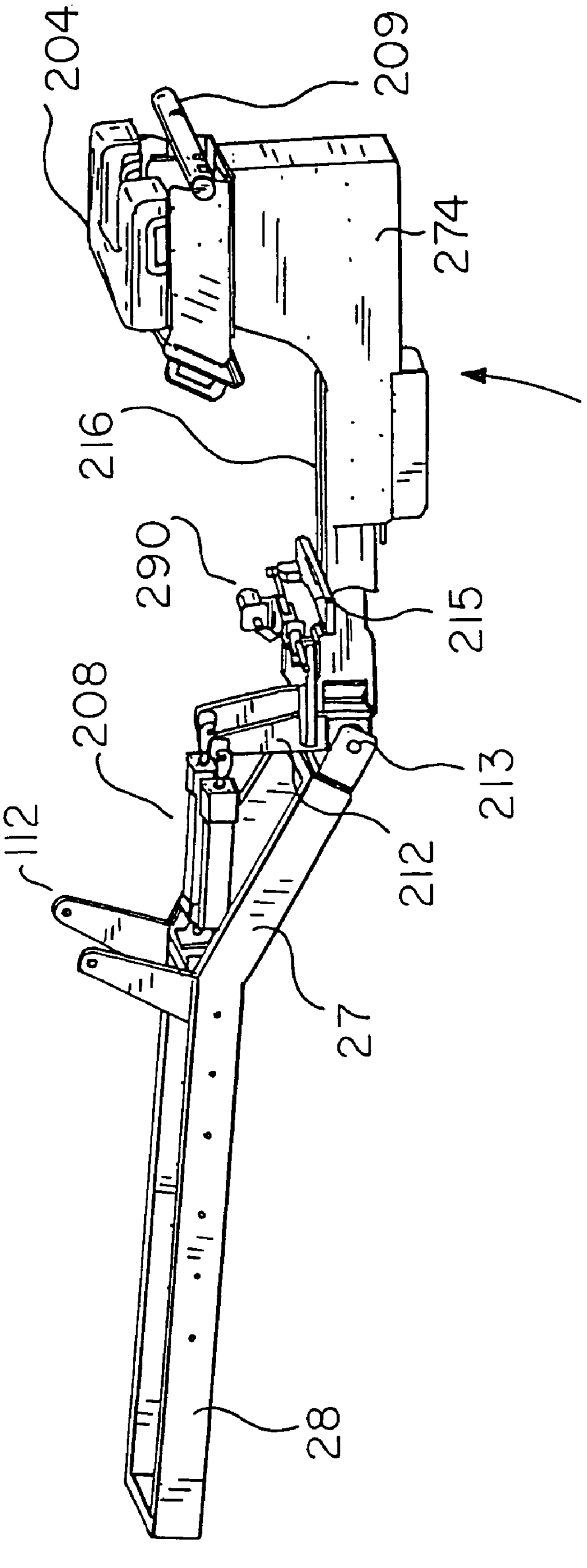
FIG. 5 is a view, similar to that of FIG. 4, however showing the foot support portion elevated relative to the lumbar assembly.

The calf/foot support assembly 200 is shown in a raised position in FIG. 5. Therein the vertical-positioning hydraulic rods 208 are shown fully retracted, the same corresponding the upper limit of the vertical position of the assembly.

Figure 6:
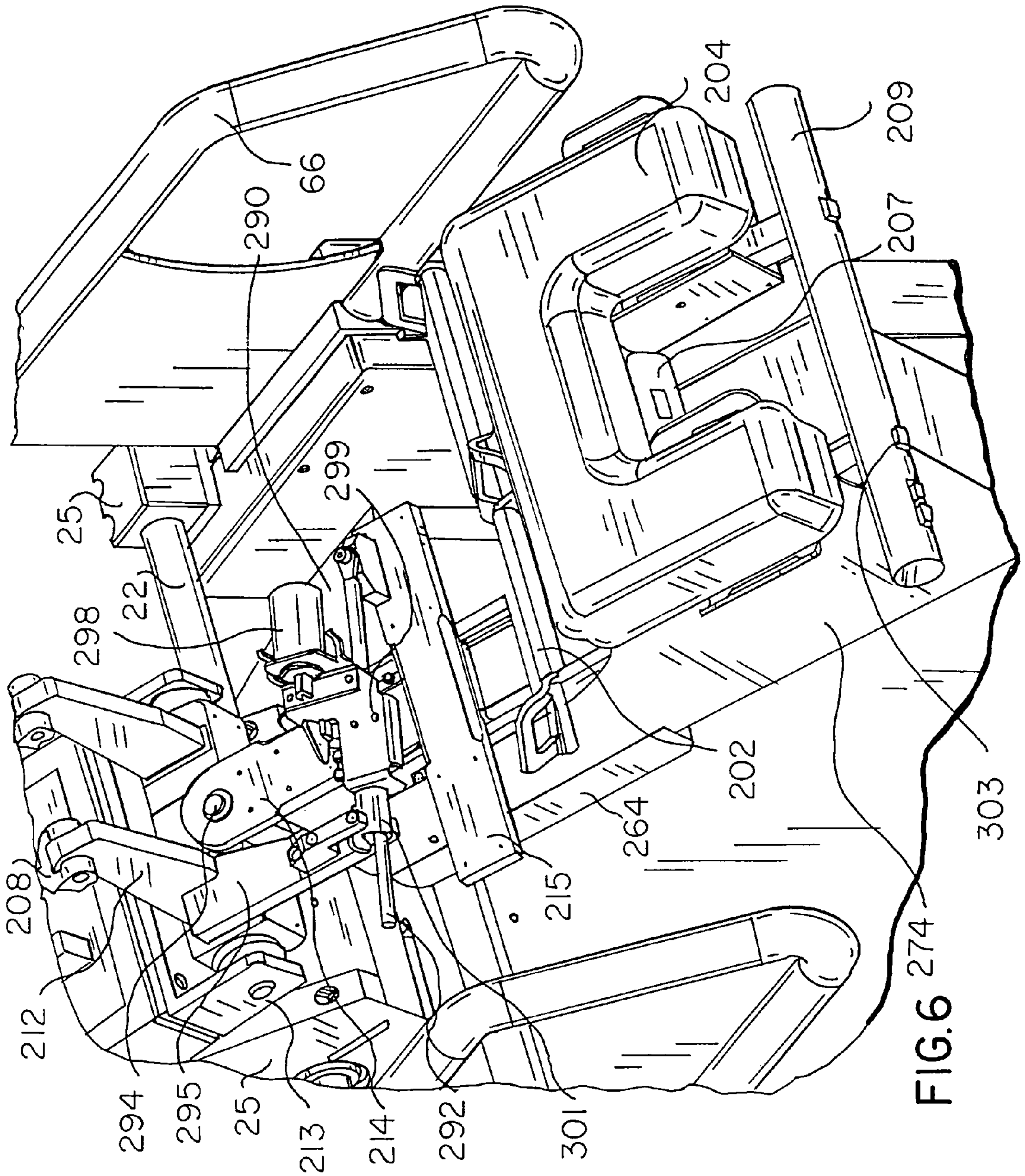
FIG. 6 is a general view of calf and foot support assembly in which the mid section covers are removed, and showing the side-swing motion mechanism of the system.

In FIG. 6 is shown a general view of the calf/foot support assembly in which the mid-section covers thereof have been removed. It is noted that the subassemblies of the calf/foot support assembly rest upon foot tubing 214 (see also FIG. 5) that is pivotally attached for the calf/foot support link casting 212, which itself is pivotally attached to the rigid support platform (see axial 213) for vertically positioning, thereby permitting the calf/foot support assembly to be lifted up to 30° above the horizontal plane of lower part 30 and as much as 15° therebelow.

Further shown in FIG. 6 are side handles 66 of the system and, with respect to sided-swing assembly 290, there is shown transverse bar 215, vertical pivot axle 294 which attaches foot support assembly 200 to foot tubing 214, side-swing solenoid 298, and solenoid journal plate 299. Accordingly, upon actuation of the side-swing solenoid 298 by control 303 of the calf/foot support assembly control bar 209, journal plate 299 is rotated to the left upon side swing control bar 292 and, therewith, the calf/foot support assembly 200.

Figure 7:
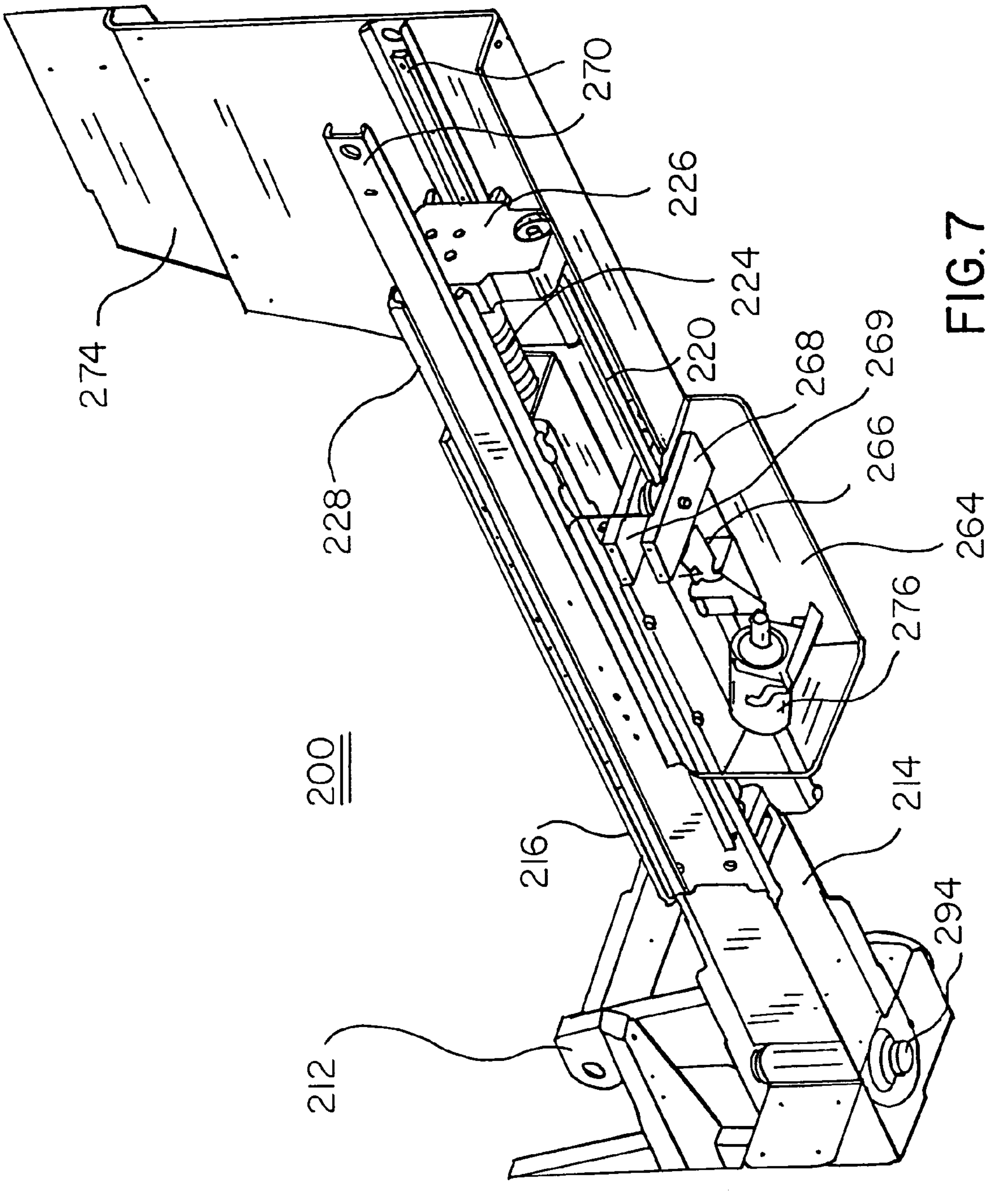
FIG. 7 is a bottom view of the calf and foot support assembly showing the foot-lock housing thereof attached to the foot side brackets.

In FIG. 7 is shown the bottom view of the assembly 200 inclusive of foot side brackets 274. In said figure a foot mechanical lock 266 is fixed to foot lock housing 264 by two mechanical lock brackets 268 and 269. A mechanical lock rod 220 is rigidly screwed onto a thrust plate 226 of the assembly 200. When mechanical lock solenoid 276 is activated, said foot mechanical lock 266 is released from mechanical lock rod 220, permitting foot-lock housing 264 to slide along the mechanical lock rod 220, thereby adjusting the overall length of the calf/foot support assembly 200, to accommodate different patient heights before the assembly is locked into position. During powered foot traction operation of the system, hydraulic rod 221, spring assembly 224, thrust plate 226 and the entire foot side bracket group 260 (in FIG. 11), move in unison.

Figure 8:
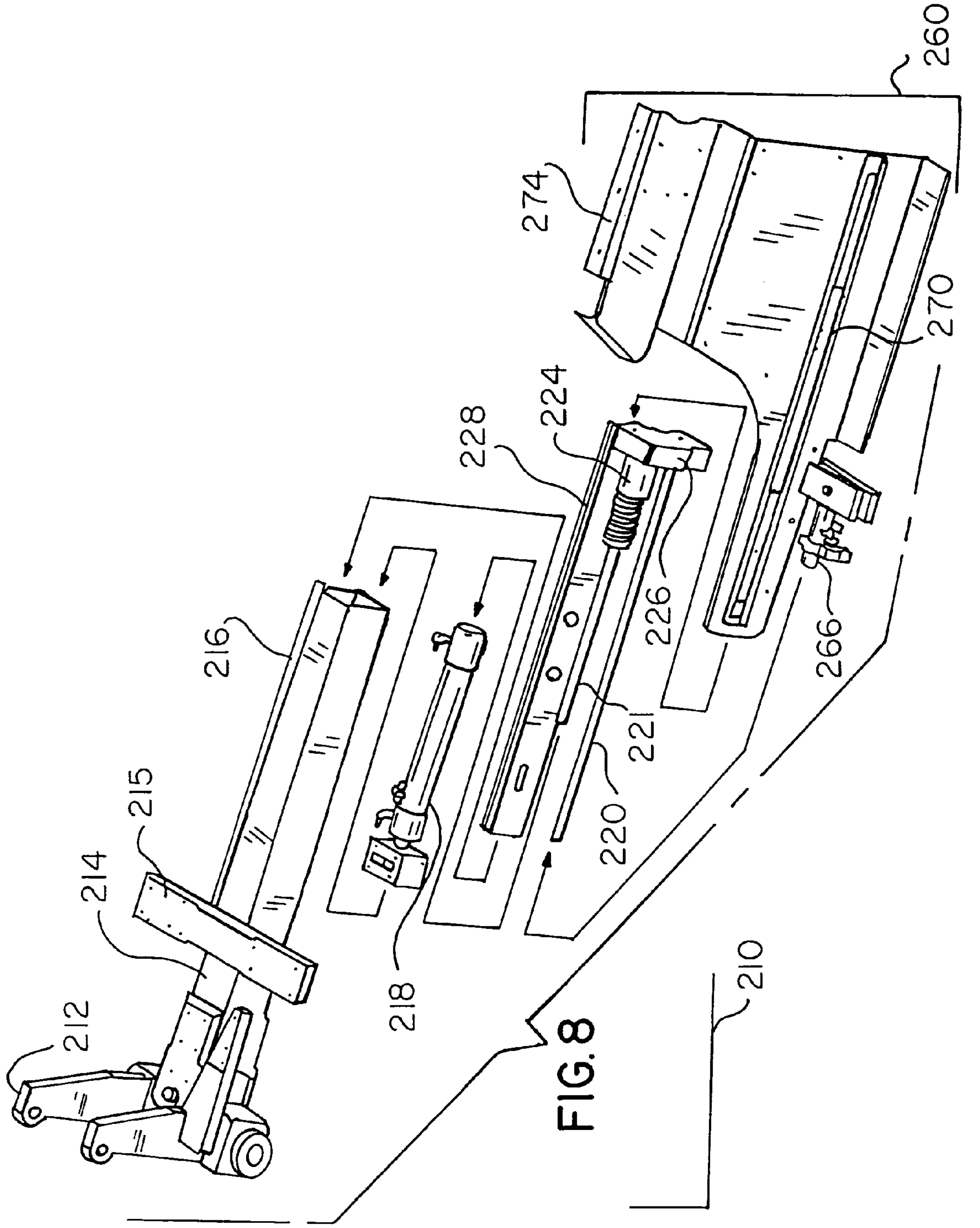
FIG. 8 is a side exploded view of the elements of calf-foot support assembly including foot tubing and foot side bracket groups of elements.

In the exploded view of FIG. 8 may be seen the front half of foot side brackets 274 and middle slides 228. Therein hydraulic cylinder 218, is mounted inside of foot tubing 214, from which hydraulic rod 221 is powered. The other end of the hydraulic rod 221 is rigidly fixed into spring assembly 224 which in turn is mounted upon thrust plate 226. Said thrust plate 226 is itself mounted on middle slides 228 for hydraulic/pneumatic linear traction. Middle slides 228 slide upon outer slides 216.

Also attached to thrust plate 226 is said mechanical lock rod 220 which extends in parallel with the rest of foot tubing group 210. Inner slides 270 of foot side bracket group 260 are inserted into said middle slides 228 to enable linear movement. Mechanical lock 266, which is fixed to foot side bracket group 260 through the housing thereof, slides along mechanical lock rod 220 as the foot side bracket group 260 moves linearly relative to the foot tubing group 210. The sliding movement of foot side bracket group 260 is used for patient height adjustment.

After mechanical lock 266 is locked upon mechanical lock rod 220, said foot side bracket group is locked relative to hydraulic rod 221 which can then be used to provide linear traction power to the foot side bracket group 260. Such power traction is linearly guided by said middle slides 228 moving into outer slides 216, as well as by the action of hydraulic cylinder 218 itself, which is a foot traction cylinder.

Figure 9:
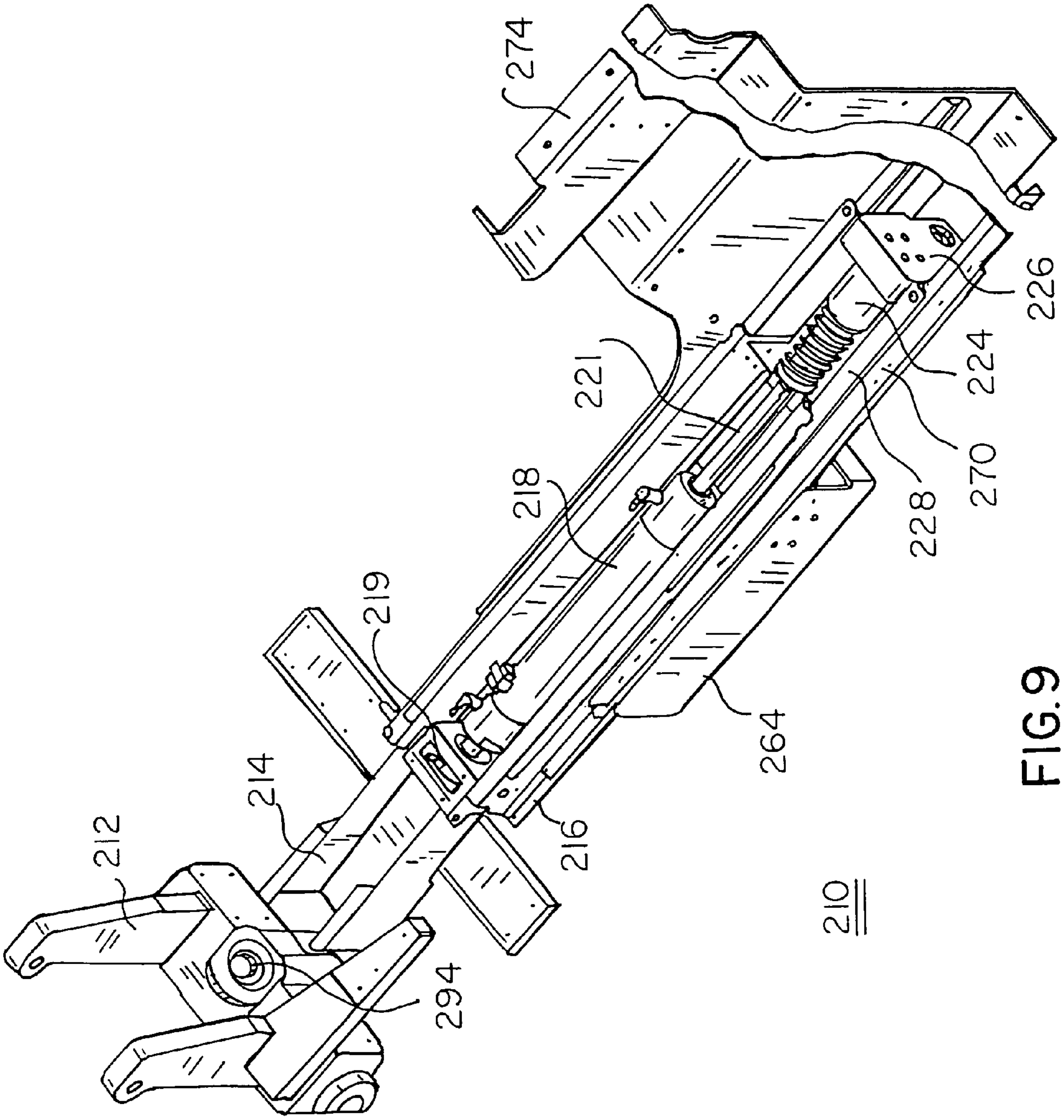
FIG. 9 is an exposed view of the interior elements of the calf and foot support assembly.

In FIG. 9 is shown an exposed view of calf/foot support assembly 200 including, particularly, the foot tubing group 210 thereof. Foot tubing 214 may be seen, revealing hydraulic cylinder 218 which is located therein. Further shown is one of foot side brackets 274. It may be further seen that hydraulic rod 221 is connected to shock absorbing spring assembly 224 that is attached to thrust plate 226 which, in turn, is mounted upon middle slides 228 upon each side thereof. Inner slides 270 are fixed to the inside of foot side brackets 274. Outer slides 216 are externally attached to the sides of foot tubing 214. Middle slides 228 and inner slides 270 are indirectly locked by a mechanical lock in the foot lock housing 264 to insure transfer of hydraulic power to the foot side brackets. Also shown in FIG. 9 is load cell 219 which monitors over-pressure conditions at a proximal output of hydraulic cylinder 218, and vertical pivot axle 294 upon which foot tubing 214 rotates.

Figure 10:
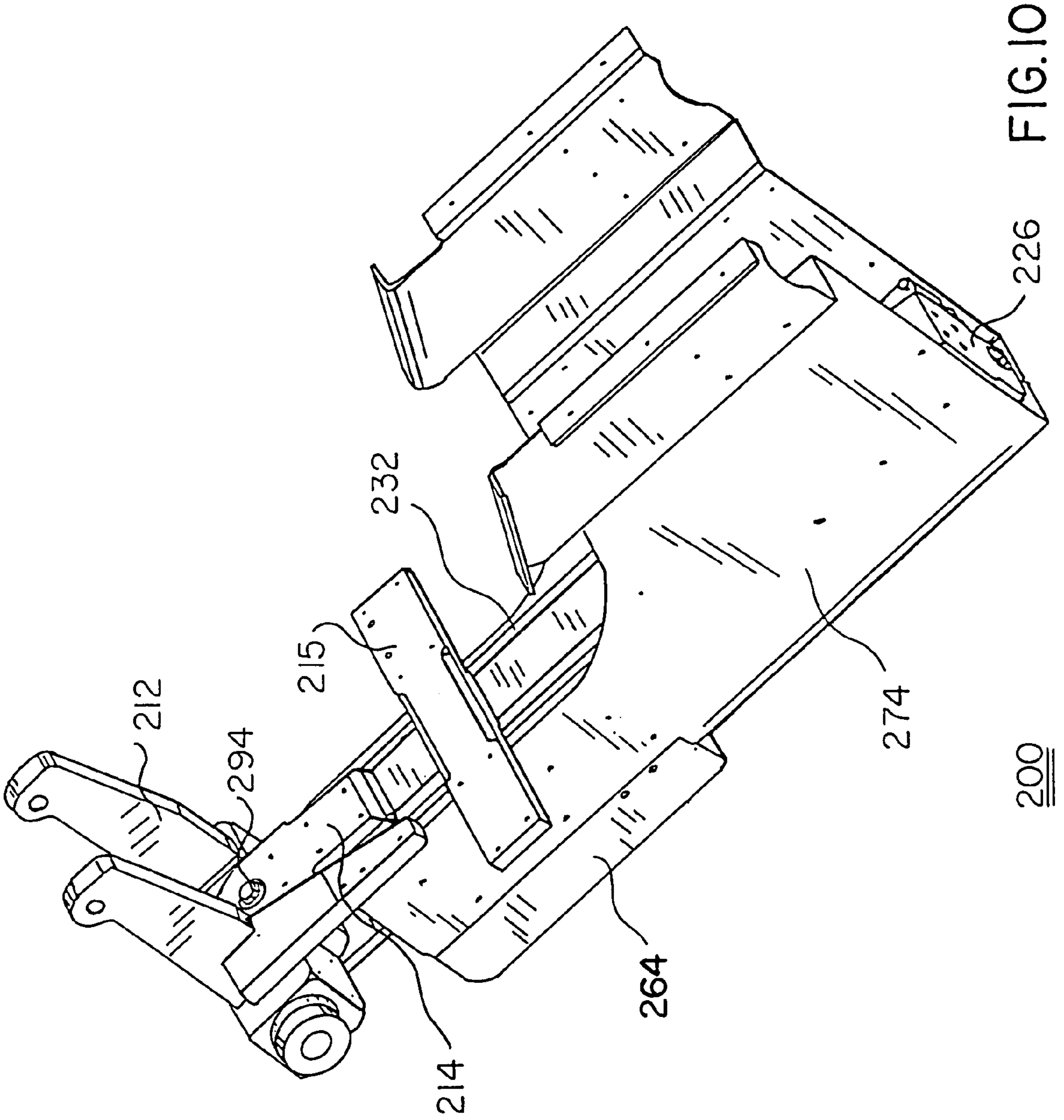
FIG. 10 is an assembly view of the major components of the calf and foot support assembly.

In FIG. 10 is shown major components of calf/foot support assembly 200 including foot/calf support link casting 212, vertical pivot axle 294, foot tubing 214, transverse bar 215, ball-bearing slide assembly 232, foot lock housing 264, foot side brackets 274, and thrust plate 226. Therein, foot tubing 214 houses a foot traction hydraulic assembly (not shown) and pivots horizontally upon vertical pivot axle 294 of foot/calf support link casting 212. Ankle cushion, foot support assembly control bar (both not shown), and ankle harnesses mount on the foot side brackets and are slidably mounted upon foot tubing 214 by ball bearing slide assembly 232. As noted in FIG. 7, a mechanical locking assembly is located inside of foot lock housing 264 and operates to unlock the main components of the foot assembly when patient height adjustment is required.

Figure 11:
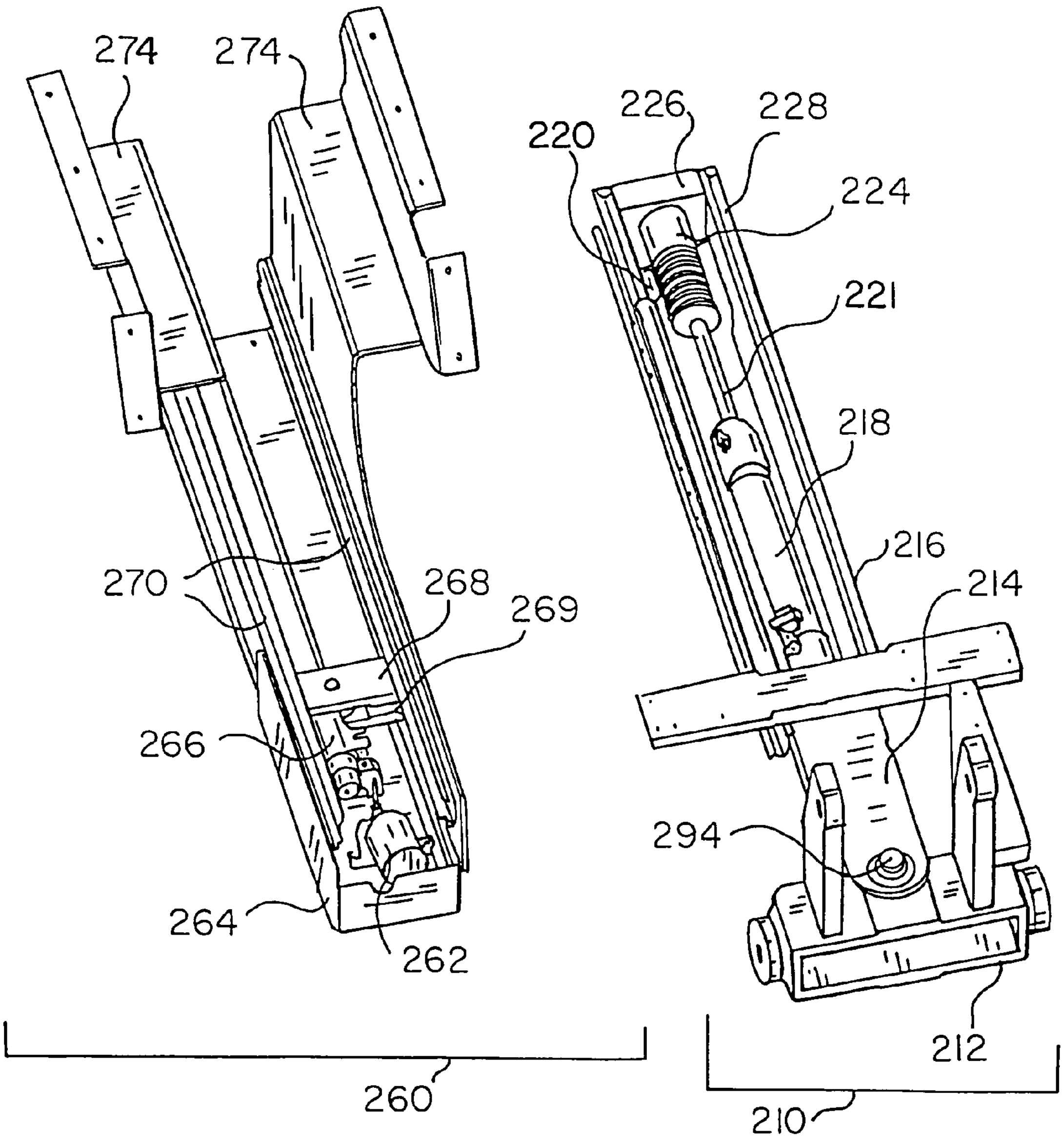
FIG. 11 are assembly views of the two major subgroups of the foot and calf support assembly.

In FIG. 11 is shown foot tubing group 210 and foot side bracket group 260. Therein, the foot side bracket group 260 is pivotally attached to the foot support link casting 212 by vertical axial 294, and houses the foot traction hydraulic assembly inclusive of hydraulic cylinder 218, hydraulic rod 221, and spring assembly 224.

Foot side bracket group 260 is slidably attached to the foot tubing group 210 by means of said inner slides 270, middle slides 228, and outer slides 216. Individual adjustments to accommodate patients heights are made by allowing mechanical lock 266 to slide upon mechanical lock rod 220, thus locking foot mechanical lock to the mechanical lock rod after an adjustment of relative position of foot side bracket group 260 to the hydraulic rod 220 of the foot tubing group 210.

Figure 12:
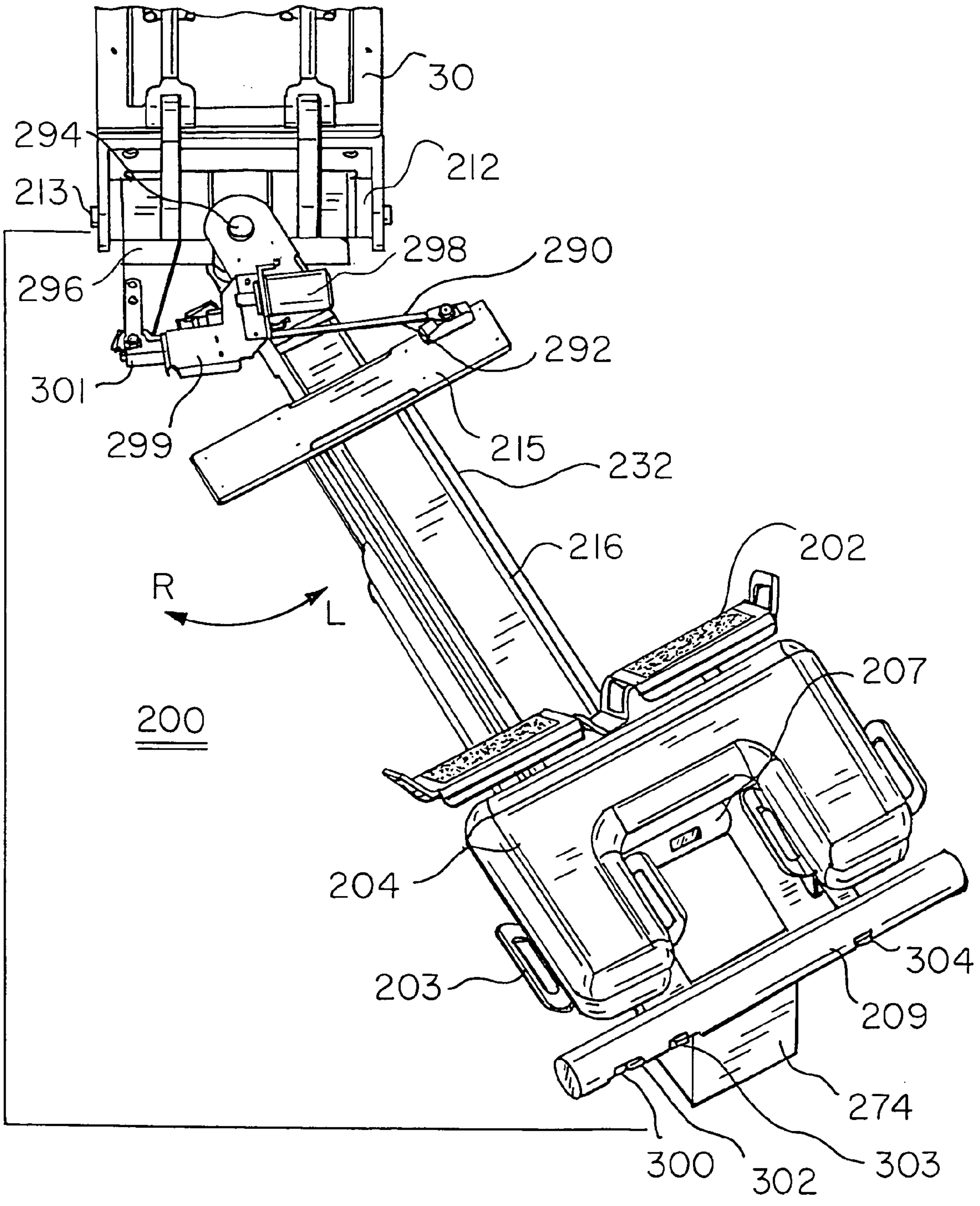
FIG. 12 is an assembly view, further to FIG. 6, of the elements associated with side-swing motion of the calf/foot support assembly.

FIG. 12, which is related to FIG. 6, is an illustration of the side-swing motion and side-swing assembly 290 of the calf/foot support assembly 200. Therein calf/foot support assembly is pivotally attached to foot/calf support link casting 212 at vertical pivot axle 294 to effect sideway (left and right) movements of the calf and leg. The side-swing assembly (described more fully above in FIG. 6) links to foot tubing 214 through vertical pivot axle 294 which connects solenoid journal plate 299 of the side-swing assembly 290 to transverse bar 215 which rests upon ball bearing slide assembly 232. (See also FIG. 10). Thereby, actuation of side-swing solenoid 298 by side motion control switch 303 will govern of the left to right motion of the foot support assembly. Once locked by side-swing mechanical lock 301, the relative side-swing angle of the calf/foot support assembly 200 relative to lower part 30 is maintained.

As also shown in FIG. 12 are the controls associated with calf/foot support assembly control bar 209, namely, power traction Y axis control switches 300 and 302 as well as patient height, Y axis adjustment switch 304. Also shown in FIG. 12 is LCD reader 207, a foot rest 202, ankle cushion 204, and ankle strap brackets 203.

It is to be understood that FIGS. 1 and 2 further illustrates a system control 74 for use by the doctor which includes the following function buttons:

| | | |
|---|---|---|
| 1. | TBL LFT = | Table Lift. |
| 2. | TBL LWR = | Table Lower. |
| 3. | ROT BACK = | Rotate Table Back. |
| 4. | ROT FWD = | Rotate Table Forward. |
| 5. | ARM UP = | Translational Arm Height Up. |
| 6. | ARM DWN = | Translational Arm Height Down. |
| 7. | OPEN | |
| 8. | OPEN | |
| 9. | ARM R. UP = | Arm Rotate Up. |
| 10. | ARM R. DOWN = | Arm Rotate Down. |
| 11. | LUM IN = | Lumbar in |
| 12. | LUM OUT = | Lumbar Out |
| 13. | OPEN | |
| 14. | OPEN | |
| 15. | RBK TL = | Rotate Table Back with Table Lift. |
| 16. | RFW TLW = | Rotate Table Forward with Table and Lower Table. |

-continued

| | | |
|---|---|---|
| 17. | SAFETY ON AND OFF = | A safety on and off button is included which stops pneumatic/hydraulic piston and ceases all table movement. |

As a safety measure, controls may also be incorporated into overhead gripping means 54 or into handgrips 42 (see FIGS. 1 and 2), with optional patient control of other functions.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention.

I claim:

1. A calf/foot support and treatment table for extension, flexion, traction, distraction, and lateral movement of the body of a patient, comprising:

(a) a base adapted to rest upon a floor;

(b) system support means having an upper end and a lower end integrally secured to said base;

(c) a rigid support platform having a lower part and an upper part, said support platform being secured to said system support means; and (d) a calf/foot support assembly transversely attached to said lower part of said support platform, said calf/foot support assembly comprising a foot tubing group which comprises a hydraulic cylinder and a hydraulic rod; a foot side bracket group attached to said foot tubing group and mechanically locked relative to said hydraulic rod; and an ankle cushion mounted on top of foot side brackets of said foot side bracket group; said hydraulic cylinder enabling a sliding movement of said foot side brackets and said ankle cushion for linear traction.

2. The calf/foot support and treatment table of claim 1, wherein said foot tubing group further comprises a spring assembly and a thrust plate mounted upon said spring assembly; and one end of said hydraulic rod is fixed into said spring assembly; thereby during a powered foot traction operation, said hydraulic rod, said spring assembly, said thrust plate and said foot side bracket group move in unison.

3. The calf/foot support and treatment table of claim 2, wherein said foot tubing group further comprises a mechanical lock, a mechanical lock solenoid and a mechanical lock rod extending in parallel with said hydraulic rod and having one end connected onto said thrust plate; wherein when said mechanical lock solenoid is activated, said mechanical lock is released from said mechanical lock rod, permitting adjusting an overall length of said calf/foot support assembly.

4. The calf/foot support and treatment table of claim 2, wherein said foot tubing group further comprises a foot tubing housing said hydraulic cylinder, outer slides attached to sides of said foot tubing, and middle slides mounted on said thrust plate; and wherein said middle slides slide upon outer slides for linear traction.

5. The calf/foot support and treatment table of claim 4, wherein said foot side bracket group comprises inner slides fixed to an inside of said foot side brackets; and said middle slides of said foot tubing group are inserted onto said inner slides for linear movement.

6. The calf/foot support and treatment table of claim 1, wherein said calf/foot support assembly further comprises a calf/foot support assembly control bar which controls power traction and patient height adjustment.

7. The calf/foot support and treatment table of claim 1, wherein said calf/foot support assembly is pivotally attached to said lower part of said support platform, enabling a vertical movement of said calf/foot support assembly in a range relative to a horizontal plane of said lower part of said support platform.

8. The calf/foot support and treatment table of claim 7, wherein said vertical movement is in a range from 30° above said horizontal plane to 15° below said horizontal plane.

9. The calf/foot support and treatment table of claim 1 further comprising a side-swing assembly permitting lateral movement of said calf/foot support assembly relative to a longitudinal axis of said support platform.

10. The calf/foot support and treatment table of claim 1 further comprising a lumbar support assembly disposed on said lower part of said support platform.

11. The calf/foot support and treatment table of claim 10 further comprising means for independent articulation and movement of said lumbar assembly.

12. A calf/foot support and treatment table for extension, flexion, traction, distraction, and lateral movement of the body of a patient, comprising:

(a) a base adapted to rest upon a floor;

(b) system support means having an upper end and a lower end integrally secured to said base, said support means including a pivot axle proximal to said upper end thereof;

(c) a rigid support platform having a lower part and an upper part, said support platform pivotally secured to said pivot axle of said system support means;

(d) a lumbar support assembly disposed on said lower part of said support platform; and (e) a calf/foot support assembly transversely attached to said lower part of said support platform, said calf/foot support assembly comprising a foot tubing group which comprises a hydraulic cylinder and a hydraulic rod; a foot side bracket group attached to said foot tubing group and mechanically locked relative to said hydraulic rod; and an ankle cushion mounted on top of foot side brackets of said foot side bracket group; said hydraulic cylinder enabling a sliding movement of said foot side brackets and said ankle cushion for linear traction.

13. The calf/foot support and treatment table of claim 12, wherein said foot tubing group further comprises a spring assembly and a thrust plate mounted upon said spring assembly; and one end of said hydraulic rod is fixed into said spring assembly; thereby during a powered foot traction operation, said hydraulic rod, said spring assembly, said thrust plate and said foot side bracket group move in unison.

14. The calf/foot support and treatment table of claim 13, wherein said foot tubing group further comprises a mechanical lock, a mechanical lock solenoid and a mechanical lock rod extending in parallel with said hydraulic rod and having one end connected onto said thrust plate; wherein when said mechanical lock solenoid is activated, said mechanical lock is released from said mechanical lock rod, permitting adjusting an overall length of said calf/foot support assembly.

15. The calf/foot support and treatment table of claim 13, wherein said foot tubing group further comprises a foot tubing housing said hydraulic cylinder, outer slides attached to sides of said foot tubing, and middle slides mounted on said thrust plate; and wherein said middle slides slide upon outer slides for linear traction.

16. The calf/foot support and treatment table of claim 15, wherein said foot side bracket group comprises inner slides fixed to an inside of said foot side brackets; and said middle slides of said foot tubing group are inserted onto said inner slides for linear movement.

17. The calf/foot support and treatment table of claim 12, wherein said calf/foot support assembly further comprises a calf/foot support assembly control bar which controls power traction and patient height adjustment.

* * * * *